United States Patent [19]

Miyoshi

[11] Patent Number: 5,252,304

[45] Date of Patent: Oct. 12, 1993

[54] FORMALIN STERILIZATION APPARATUS

[75] Inventor: Tetsuo Miyoshi, Kamagaya, Japan

[73] Assignee: Mercian Corporation, Tokyo, Japan

[21] Appl. No.: 781,382

[22] Filed: Oct. 23, 1991

[30] Foreign Application Priority Data

Oct. 26, 1990 [JP] Japan ............................ 2-289487

[51] Int. Cl.$^5$ .............................................. A61L 2/20
[52] U.S. Cl. ......................................... 422/305; 422/28; 422/30; 422/36; 422/306
[58] Field of Search ................ 422/28, 30, 36, 305, 422/306

[56] References Cited

U.S. PATENT DOCUMENTS

| | | | |
|---|---|---|---|
| 3,898,038 | 8/1975 | Anderson | 422/306 X |
| 4,119,400 | 10/1978 | Kurz | 422/306 X |
| 4,241,020 | 12/1980 | Grantham | 422/109 |
| 4,973,449 | 11/1990 | Kolstad et al. | 422/27 |

FOREIGN PATENT DOCUMENTS

| | | | |
|---|---|---|---|
| 773391 | 1/1972 | Belgium . | |
| 0237836 | 9/1987 | European Pat. Off. . | |
| 2331359 | 1/1975 | Fed. Rep. of Germany | 422/36 |
| 2335240 | 7/1977 | France . | |
| 2352551 | 12/1977 | France . | |
| 2555452 | 5/1985 | France . | |
| 2612780 | 9/1988 | France | 422/36 |
| 0152563 | 9/1983 | Japan | 422/36 |
| 64-928 | 1/1989 | Japan . | |
| 64928 | 1/1989 | Japan . | |
| 737893 | 10/1955 | United Kingdom | 422/36 |
| 1350301 | 4/1974 | United Kingdom | 422/36 |
| 2164258 | 3/1986 | United Kingdom . | |

OTHER PUBLICATIONS

JP59051786, English Abstract, Mar. 1984.

Primary Examiner—Robert J. Warden
Assistant Examiner—Stephanie Smith
Attorney, Agent, or Firm—Cushman, Darby & Cushman

[57] ABSTRACT

A reaction chamber is disposed between a heating chamber and an outlet line of the heating chamber, and performs a reaction of ammonia gas vaporized in the heating chamber with formaldehyde circulated from a room to be sterilized. A filter is disposed between the reaction chamber and the outlet line.

6 Claims, 3 Drawing Sheets

FORMALIN STERILIZATION APPARATUS

BACKGROUND OF THE INVENTION

The present invention relates to a formalin sterilization apparatus for sterilizing, using formalin, an entire room such as an operation room or a patient's room in a hospital, for example.

A formalin sterilization apparatus of the type mentioned above is disclosed, for example, in Japanese Utility Model Publication sho 64-928. As shown in FIG. 3, this apparatus has a formalin container(31) and an ammonia water cotainer(35) which are connected to a heating chamber(34) by respective lines(33,37) provided with respective solenoid valves(32,36). Said heating chamber(34) is provided with a heater(38) and a vaporizing heater(39) for generating formaldehyde or ammonia gas. The heating chamber(34) is connected to a room(43) to be sterilized by a line(41) having a fan(40) and a bellows(42), and connected to said room(43) by another line(46) having a valve(47) and another bellows(45). A line(48) is divided from said line(46) at an upstream point of said valve(47) and communicated with the atmosphere via a valve(49) and an activated carbon container(50); a line(51) is divided from the line(46) at a downstream point of the valve(47) and communicated with the atmosphere via a valve(52) and a filter(53).

To perform sterilization and neutralization with formalin by this apparatus, first, the solenoid valve(36) and the valves(49,52) are closed and the solenoid valve(32) and the valve(47) are opened in order to feed formalin from the formalin cotainer(31) to the heating chamber(34). Formalin in the heating chamber(34) is then heated by the heaters(38,39) and vaporized into formaldehyde. This formaldehyde is fed by the fan(40) into the room(43) to be sterilized through the line(41) and the bellows(42) and is circulated to the heating chamber(34) through the bellows(45) and the line(46), thereby sterilizing the room(43) (sterilizing process).

The solenoid valve(32) and the valve(47) are then closed and the valves(49,52) are opened to feed clean air through the filter(53) into the the room(43), so that the formaldehyde in the room(43) is replaced by clean air. The exiting formaldehyde is passed through the activated carbon container(50) to be made harmless, and to be exhausted into the atmosphere (exhausting process).

The valves(49,52) are then closed and the solenoid valve(32) and the valve(47) are opened to feed ammonia water from the ammonia water cotainer(35) into the heating chamber(34), where the ammonia water is vaporized into ammonia gas by the heaters(38,39). Next, this ammonia gas is fed, by the fan (40), into the room(34), through the line(41) and the bellows(42), and then circulated to the heating chamber(34) through the bellows(45) and the line(46), thereby neutralizing formaldehyde remaining in the room(34) and in objects therein (neutralizing process). The ammonia gas is then exhausted into the atmosphere in the same way as in the previously mentioned exhausting process.

The apparatus as described above is, however, adapted to replace, in the exhausting process (after the formaldehyde sterilization process), formaldehyde in the room to be sterilized by clean air containing no bacterium or the like. For this reason the apparatus must have, in addition to a system for generating and circulating formaldehyde, a separate system including a filter and a line for intrducing clean air, and valves for switching these systems; it is therefore complicated in structure.

Also, because the prior apparatus is not adapted to precisely control the amount of formalin and ammonia water in the heating chamber, and the vaporizing temperature thereof, the formalin and ammonia water can overflow the heating chamber, or the amounts and temperatures of the generated formaldehyde and ammonia gas, for example, are not uniform and this has an adverse effect on the sterilizing and neutralizing actions.

SUMMARY OF THE INVENTION

Accordingly, it is an object of the present invention to provide a formalin sterilization apparatus which has a comparatively simple structure for maintaining a room to be sterilized in a clean state and which can also precisely control the amount and temperature of the generated formaldehyde or ammonia gas.

In accordance with the present invention, this and other objects are achieved by providing a formalin sterilization apparatus which comprises a heating chamber connected to a room to be sterilized by an inlet line and an outlet line; a formalin container and an ammonia water container for selectively supplying formalin or ammonia water to the heating chamber; a heater for heating the formalin or ammonia water selectively supplied to the heating chamber to generate formaldehyde or ammonia gas; a fan for circulating the generated formaldehyde and ammonia gas between the room or the heating chamber; a reaction chamber between the heating chamber and the outlet line for Performing the reaction of the ammonia gas vaporized in the heating chamber with the formaldehyde circulated from the room; and a filter disposed between the reaction chamber and the outlet line.

BRIEF DESCRIPTION OF THE DRAWINGS

A formalin sterilization apparatus according to the present invention will be described hereinafter in more detail with reference to the accompanying drawings, in which.

DETAILED DESCRIPTION OF THE PREFERRED EMBODIMENTS

Figure 1:
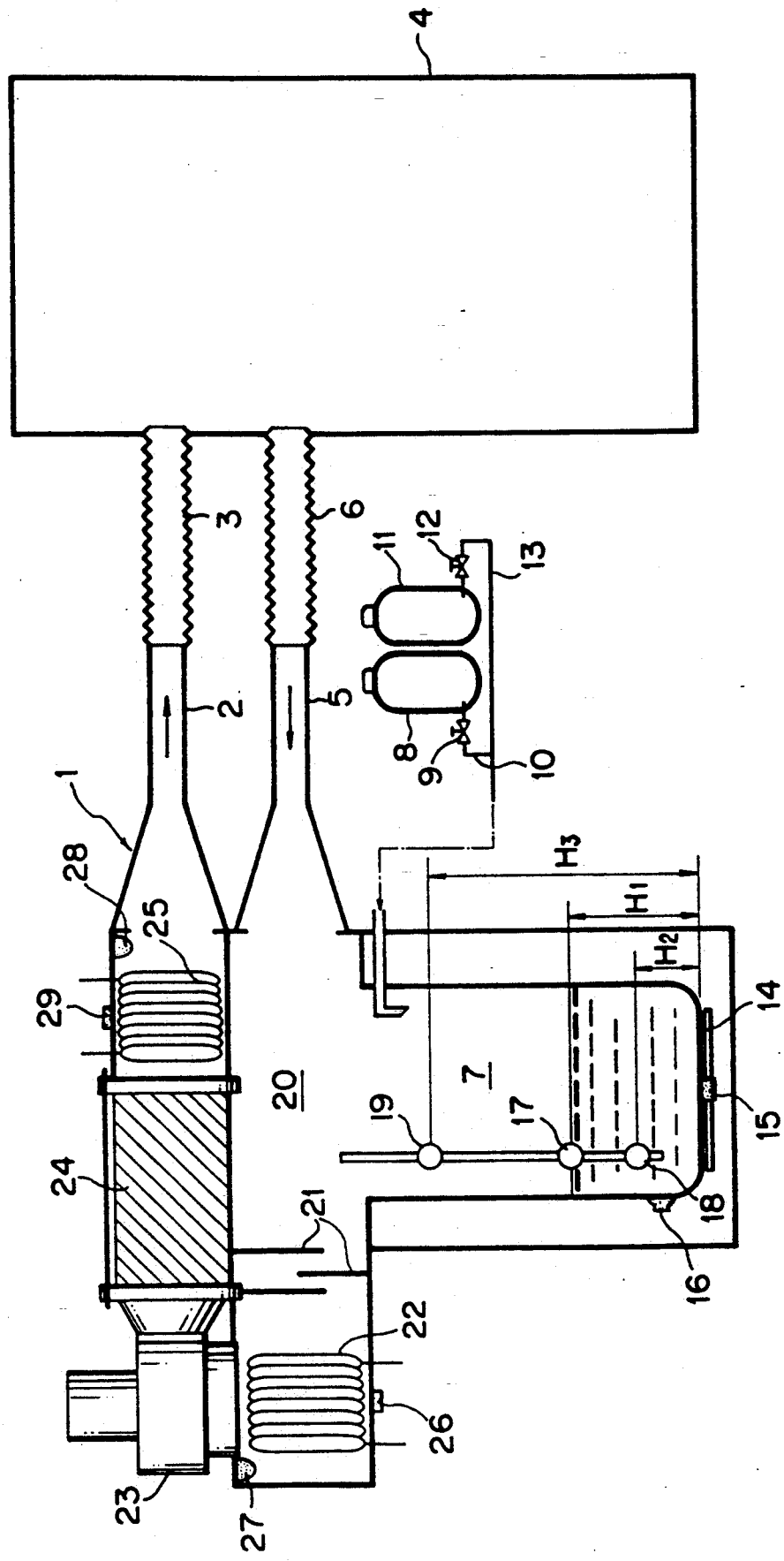
FIG. 1 is a schematic illustration of a whole construction of a formalin sterilization apparatus, according to the present invention, and a room to be sterilized.

FIG. 1 shows a formalin sterilization apparatus according to the present invention (hereinafter merely referred as "apparatus"). The apparatus is, as indicated at 1, adapted to be connected, to an inlet of a room 4 to be sterilized, by an outlet line 2 and a flexible bellows 3, and to an outlet of the room 4, by an inlet line 5 and a flexible bellows 6.

The apparatus 1 has a heating chamber 7. A formalin container 8 and an ammonia water container 11 are connected to the heating chamber 7 through a solenoid valve 9 and a line 10, and through a solenoid valve 12 and a line 13, respectively, so that formalin and ammonia water can be selectively supplied from these containers 8 and 11 to said heating chamber 7. A primary heater 14 is provided on the bottom of the heating chamber 7 and heats and vaporizes the formalin or ammonia water supplied to the heating chamber 7 to generate formaldehyde or ammonia gas. This primary heater 14 is provided with an overheat-preventing sensor 15. This sensor 15 is adapted to stop the primary heater 14 when sensing a temperature higher than a predetermined temperature (for example, 150° C.), thereby preventing the primary heater 14 from overheating. Said overheat-preventing sensor 15 is also adapted to sense a temperature rise when the heating chamber 7 becomes nearly empty, thereby preventing the heating chamber 7 from being heated in the empty state. Also, a temperature control sensor 16 for ammonia water is disposed on the heating chamber 7 at a lower portion of the outside thereof. This sensor 16 is variable in preset temperature and is adapted to actuate/stop the primary heater 14 based on the preset temperature, so as to maintain the vaporizing temperature of the ammonia water at a predetermined temperature slightly higher than the boiling point of ammonia.

In order to regulate liquid levels in the heating chamber 7, three float level sensors 17, 18 and 19 are disposed therein along the vertical direction. The intermediate sensor 17 is a float level sensor for formalin. When sensing a level of formalin higher than a preset level $H_1$, the sensor 17 closes the solenoid valve 9 for the formalin container 8 so as to maintain the formalin at the preset level $H_1$. Similarly, the lower sensor 18 controls the solenoid valve 12 for the ammonia water container 11 so that ammonia water is maintained at a second preset level $H_2$ lower than the preset level $H_1$. The upper sensor 19 backs up the sensors 17 and 18 by maintaining the formalin and the ammonia water in the heating chamber 7 at a third preset level $H_3$, thereby preventing them from overflowing the heating chamber 7.

A reaction chamber 20 is defined at the upper portion of the heating chamber 7 by radially enlarging this heating chamber portion. Said inlet line 5 is connected to an inlet of the reaction chamber 20. A plurality of baffle plates 21 are alternatingly disposed near the outlet of the reaction chamber 20 opposite to the inlet thereof. As described below, in this reaction chamber 20, the ammonia gas generated in the heating chamber 7 is made to react with the formaldehyde circulated from the room 4 in the neutralizing process.

A secondary heater 22, a fan 23, a filter 24 and a tertiary heater 25 are disposed between an outlet of the reaction chamber 20 and said outlet line 2. The secondary heater 22 re-heats, to a predetermined temperature, the gas discharged from the heating chamber 7 and is provided with an overheat-preventing sensor 26 for preventing overheating of said secondary heater 22. The fan 23 is heat-resistant. Between this fan 23 and the secondary heater 22 is disposed a temperature control sensor 27 for protecting the fan 23 and for preventing the filter 24 from clogging. The filter 4 is mounted removably in the apparatus 1 and heat-resistant to temperatures lower than, for example, 250° C. Said filter 24 is a conventional filter referred to as an absolute filter or an HEPA filter, which can eliminate particles larger than 0.3 µm so as to eliminate bacterium. The tertiary heater 25 is provided with a temperature control sensor 28 variable in preset temperature and a overheat-preventing sensor 29 for preventing overheating of said tertiary heater 25. The tertiary heater 25 controls the final temperature of the gas blowing into the room 4 to a predetermined temperature.

The apparatus thus constituted operates in the following order: formalin vaporizing process, retaining process and neutralizing process, as described below.

Prior to operation, the formalin and the ammonia water containers 8 and 11 are filled with a predetermined amount of formalin and ammonia water, respectively and the bellows 3 and 6 are connected to the inlet and to the outlet of the room 4 to be sterilized, respectively.

(1) Formalin Vaporizing Process

First the solenoid valve 9 is opened, the solenoid valve 12 is closed, and the heaters 14, 22 and 25 and the fan 23 are actuated. Additionally, the float level sensors 17 and 19 are actuated and the float level sensor 18 is stopped. In this manner, formalin is caused to flow from the formalin container 8 through the solenoid valve 9 and the line 10 into the heating chamber 7, where it is heated by the primary heater 14 in order for the formalin to be vaporized into formaldehyde. This formaldehyde is then fed by the fan 23 through the reaction chamber 20, the secondary heater 22, the filter 24, the tertiary heater 25, the outlet line 2, the bellows 3 and lastly into the room 4. The formaldehyde is then returned to the heating chamber 7, via the bellows 6 and the line 5, and recirculated together with new formaldehyde generated in the heating chamber 7.

Figure 2:
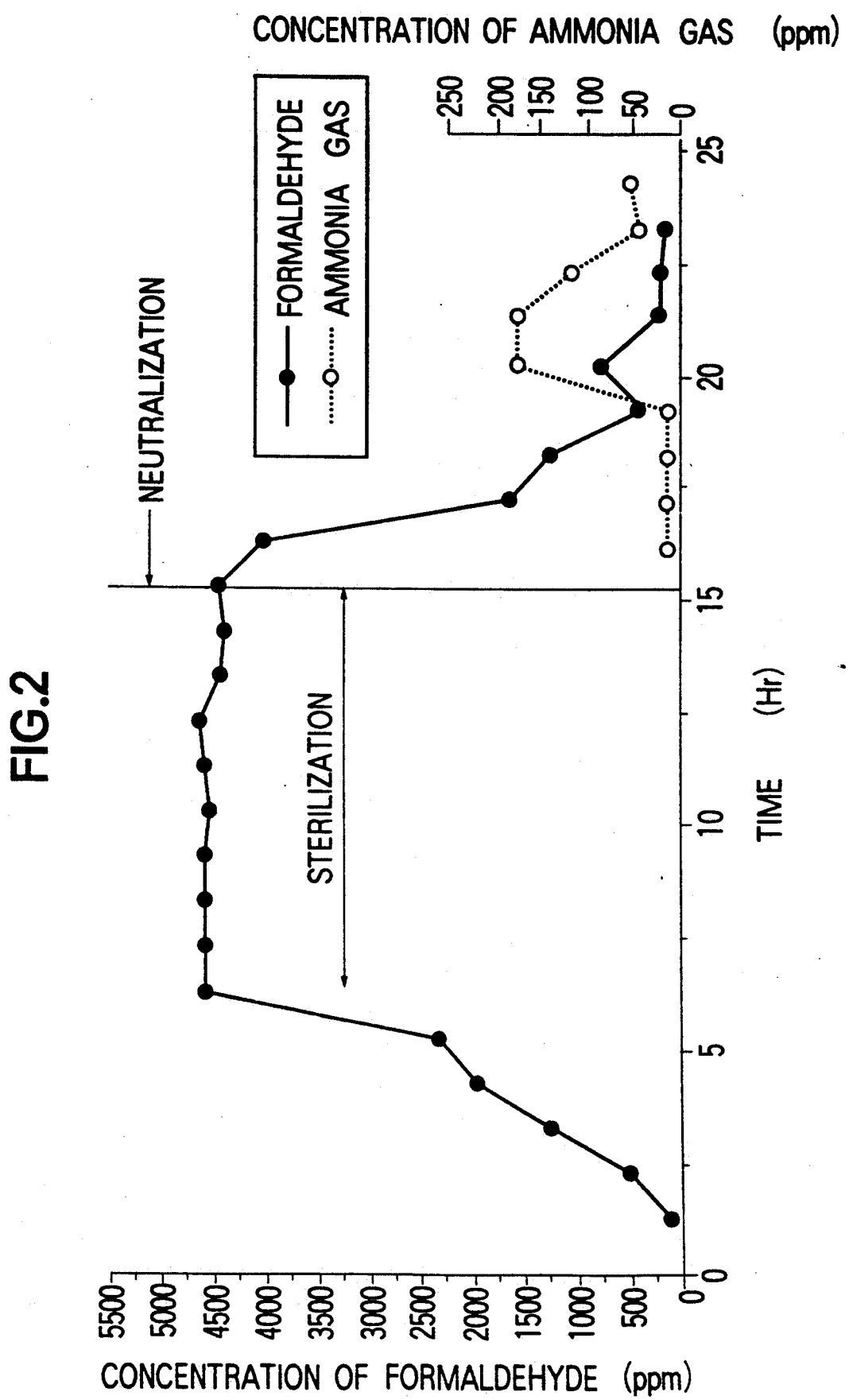
FIG. 2 is a graph showing change, with operation of the apparatus of FIG. 1, of concentration of formaldehyde and ammonia gases in the room to be sterilized.
Figure 3:
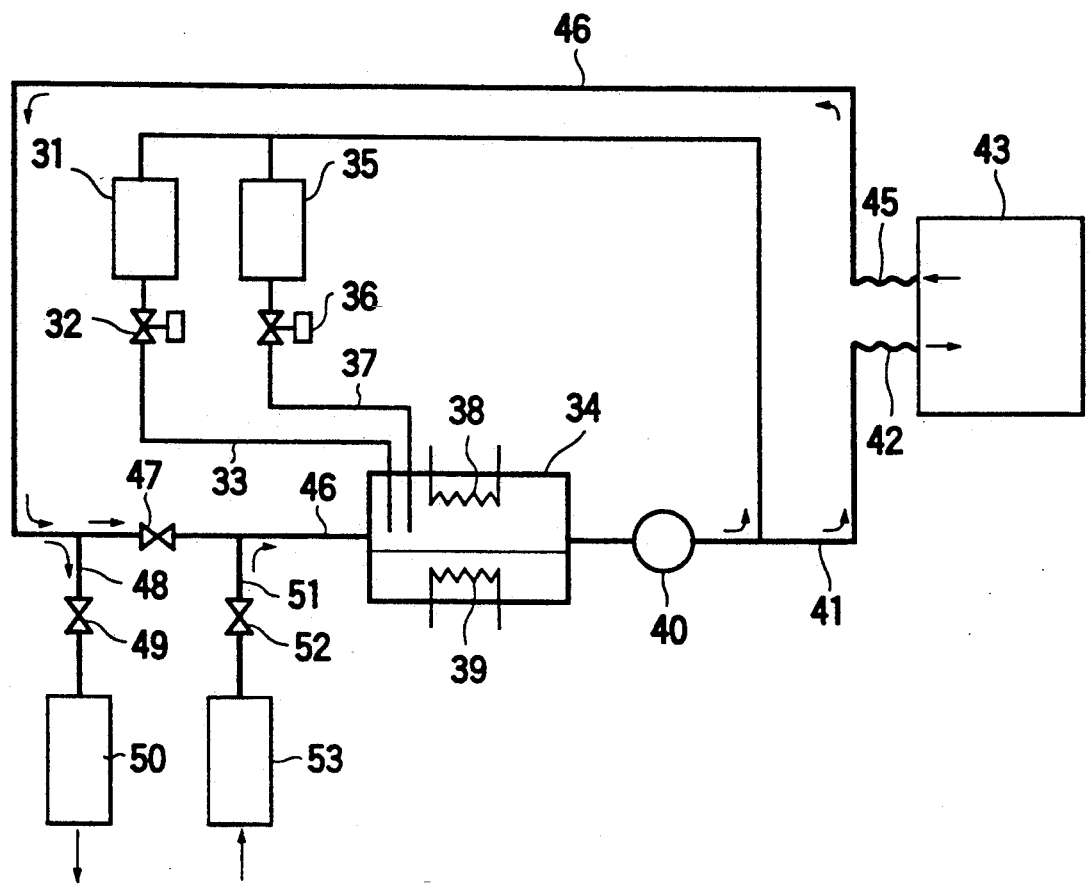
FIG. 3 is a schematic illustration of a conventional formalin sterilization apparatus and a room to be sterilized.

Continuation of such circulation, as detailed above, causes air in the heating chamber 7 to be replaced by formaldehyde and, as shown in FIG. 2, the concentration of formaldehyde in the room 4 is progressively raised. When the formalin in the formalin container 8 is consumed and the heating chamber 7 becomes near empty, the overheat-preventing sensor 15 senses the resultant rise in temperature, stops the primary heater 14 and closes the solenoid valve 9, thus completing the present process.

In the present process, because formalin in the heating chamber 7 is maintained at the preset level $H_1$ by the float level sensor 17, a large amount of formaldehyde can be stably generated. Also, in case of failure of the float level sensor 17, the formalin in the heating chamber 7 is maintained at a level lower than the preset level $H_3$ by the float level sensor 19, thereby preventing the formalin from overflowing the heating chamber 7.

Furthermore, the vaporizing temperature of formalin can be maintained at a desired temperature (for example, 80°~95° C.) slightly higher than the boiling point of formalin due to the fact that the formalin in the heating chamber 7 is maintained at preset level $H_1$ and to the relationship between preset level $H_1$ and the capability of the primary heater 14. In addition, because the formaldehyde is reheated to a predetermined temperature by means of the secondary heater 22 and the temperature control sensor 27, the filter 24 is prevented from being clogged as a result of condensation of formaldehyde. The filter 24 captures non-sterilized bacterium and the like, contained in the air circulated from the room 4, so as to prevent such bacterium from flowing into the room 4. Furthermore, the temperature of the formaldehyde blowing into the room 4 is maintained, by the tertiary heater 25 and the temperature control sensor 28, at an optimal temperature range (for example, 60°~80° C.) so that the formaldehyde can permeate the room 4 and can not be condensed by cooling.

(2) Retaining Process

The state of operation of the apparatus 1, as described above, is retained for a predetermined time. That is, by continuing to operate the fan 23 and the secondary and tertiary heaters 22 and 25, circulation of formaldehyde is continued so that formaldehyde in the room 4 can be maintained at a high concentration and thus sterilize the room 4.

(3) Neutralizing Process

The solenoid valve 12 is then opened and the primary heater 14 is actuated. Also, the float level sensors 18 and 19 are actuated and the float level sensor 17 is stopped. In this manner, ammonia water is caused to flow from the ammonia water container 11 through the solenoid valve 12 and the line 13 into the heating chamber 7, where it is heated by the primary heater 14 in order to be vaporized into ammonia gas. This ammonia gas is then mixed, in the reaction chamber 20, with the formaldehyde circulated from the room 4 in order to neutralize the formaldehyde. During this neutralization process, the baffle plates 21 of the reaction chamber 20 serve to promote the neutralization reaction since they ensure longer residence time of the formaldehyde and ammonia gases in the reaction chamber 20, and promote turbulence thereof. This mixed gas together with neutralization reaction products are then heated to a predetermined temperature, when passing through the secondary heater 22, and fed to the filter 24. If reaction products such as urotropin, cinders and the like are produced by the neutralization, they are captured by the filter 24 and prevented from flowing into the room 4. In this manner, because the neutralization of formaldehyde with ammonia is performed in the reaction chamber 20 rather than in the room 4 to be sterilized, the amount of urotropin produced in the room 4 can be significantly reduced. Said mixed gas is then heated to a predetermined temperature by the tertiary heater 25 and fed through the outlet line 2 and the bellows 3 into the room 4, where a portion of the gas neutralizes a portion of the formaldehyde and the remaining gas is replaced by the formaldehyde. This formaldehyde is returned through the bellows 6 and the inlet line 5 to the heating chamber 7 and neutralized with new ammonia gas generated in the heating chamber 7.

In the present process, because ammonia water in the heating chamber 7 is maintained, by the float level sensor 18, at preset level $H_2$ lower than preset level $H_1$ for formalin in the vaporizing process, that is, an amount of heated ammonia water is small and constant, ammonia gas can be rapidly generated by heating and the amount thereof can be made constant. Also, because the vaporizing temperature of ammonia is maintained, by the temperature control sensor 16, at a predetermined temperature (for example, 50° C.) which is lower than the vaporizing temperature of formalin and slightly higher than the boiling point of ammonia, ammonia gas is generated little by little so that it can sufficiently react with formaldehyde in the reaction chamber 20 before being fed to the filter 24. The present process is similar to the formalin vaporizing process described above in that overflowing is prevented by the float level sensor 17 and that a final temperature of the circulating gas is maintained at a predetermined temperature by the tertiary heater 25.

With continued circulation of ammonia gas, the neutralization of formaldehyde progresses and, as shown in FIG. 2, the concentration of formaldehyde in the room 4 is progressively lowered. When the ammonia water in the ammonia water container 11 is consumed and the heating chamber 7 becomes near empty, the overheat-preventing sensor 15 senses the resulting rise in temperature and stops the primary heater 14 and closes the solenoid valve 12, thus completing the present process.

Further, the present invention can be carried out in various manners other than as specifically described herein. For example, although in the embodiments described above the heating chamber for formalin and the heating chamber for ammonia water are common to one another, these chambers may be separately provided and the reaction chamber may be defined to be at the upper portion of the heating chamber for ammonia water.

As has been described, a formalin sterilization apparatus according to the present invention has a comparatively simple structure for maintaining a room to be sterilized in a clean state and can also precisely control the amounts and temperatures of generated formaldehyde and ammonia gases.

What is claimed is:

1. A formalin sterilization apparatus comprising:
   a heating chamber capable of being connected to a room to be sterilized, said heating chamber including an inlet conduit and an outlet conduit,
   a formalin container for storing formalin,
   an aqueous ammonia container for storing aqueous ammonia,
   supply means for selectively supplying formalin or aqueous ammonia from said formalin container or said aqueous ammonia container to said heating chamber,
   first heating means for heating formalin or aqueous ammonia supplied from said formalin container or said aqueous ammonia container and contained in said heating chamber so as to generate formaldehyde or ammonia gas,
   blower means for circulating said formaldehyde or said ammonia gas generated by said first heating means between said heating chamber and said room to be sterilized, said blower means being disposed between a second heating means and a filter means,
   a reaction chamber defined at an upper portion of said heating chamber and adapted for causing the ammonia gas generated by said first heating means to react with the formaldehyde fed from said room to be sterilized via said inlet conduit,
   said second heating means being disposed between said reaction chamber and said blower means and adapted for heating the formaldehyde or the ammonia gas,
   said filter means being disposed between said blower means and said outlet conduit and adapted for capturing bacteria, products produced by neutralization between the formaldehyde and the ammonia gas and the like, and
   third heating means disposed between said filter means and said outlet conduit and adapted to heat the formaldehyde or the ammonia gas.

2. A formalin sterilization apparatus in accordance with claim 1 wherein said reaction chamber is provided with a plurality of baffle plates alternatingly disposed therein.

3. A formalin sterilization apparatus in accordance with claim 1 further comprising first control means, which includes first float level sensor means for detecting a surface level of formalin contained in said heating chamber and first valve means connected to said formalin container, for controlling an amount of formalin in said heating chamber and second control means, which includes second float level sensor means for detecting a surface level of aqueous ammonia contained in said heating chamber and second valve means connected to said aqueous ammonia container, for controlling an amount of aqueous ammonia in said heating chamber.

4. A formalin sterilization apparatus in accordance with claim 2 further comprising first control means, which includes first float level sensor means for detecting a surface level of formalin contained in said heating chamber and first valve means connected to said formalin container, for controlling an amount of formalin in said heating chamber and second control means, which includes second float level sensor means for detecting a surface level of aqueous ammonia contained in said heating chamber and second valve means connected to said aqueous ammonia container, for controlling an amount of aqueous ammonia in said heating chamber.

5. A formalin sterilization apparatus in accordance with claim 3 wherein said first float level sensor is disposed in said second float level sensor.

6. A formalin sterilization apparatus in accordance with claim 4 wherein said first float level sensor is disposed in said heating chamber at a level higher than said second float level sensor.

* * * * *